United States Patent [19]

Ziegler et al.

[11] Patent Number: 4,752,573
[45] Date of Patent: Jun. 21, 1988

[54] USE OF TETRAHYDROBIOPTERIN TO ENHANCE THE PROLIFERATIVE ACTIVITY OF INTERLEUKIN-2 ON T CELLS

[75] Inventors: Irmgard Ziegler, Munich; Udo Schwulera, Hanau; Hans Sonneborn, Heusenstamm, all of Fed. Rep. of Germany

[73] Assignees: Biotest-Serum-Institut GmbH, Frankfurt; Gesellschaft fur Strahlen-und Umweltforschung mbH, Neuherberg, both of Fed. Rep. of Germany

[21] Appl. No.: 849,595

[22] Filed: Apr. 8, 1986

Related U.S. Application Data

[63] Continuation-in-part of Ser. No. 787,891, Oct. 16, 1985, abandoned.

[30] Foreign Application Priority Data

Oct. 17, 1984 [DE] Fed. Rep. of Germany ....... 3437944

[51] Int. Cl.[4] .............................................. C12N 5/02
[52] U.S. Cl. ......................................... 435/29; 435/34; 435/35; 435/244; 530/351; 544/257; 544/258
[58] Field of Search .......................... 436/33; 530/351; 514/249, 258; 544/257, 258; 435/29, 34, 35, 244

[56] References Cited

PUBLICATIONS

Cas Chemical Abstracts Index Guide—1982, p. 1074G.
Ziegler Cancer Research 43, 5356–5359, 1983.
Huber, J. Experimental Medicine 160, pp. 310–316, (1984).
Cheever, J. of Immunology 132(5), pp. 2259–2265, (1984).

*Primary Examiner*—Sidney Marantz
*Assistant Examiner*—Robert Benson
*Attorney, Agent, or Firm*—Sprung Horn Kramer & Woods

[57] ABSTRACT

The use of pterins to increase the activity of lymphokines and other cell growth factors, and a diagnostic or theraupeutic preparation that contains pterins combined with lymphokines. Adding pterins to lymphokines can increase the activity of the lymphokines by 3 to 5 times.

4 Claims, 1 Drawing Sheet

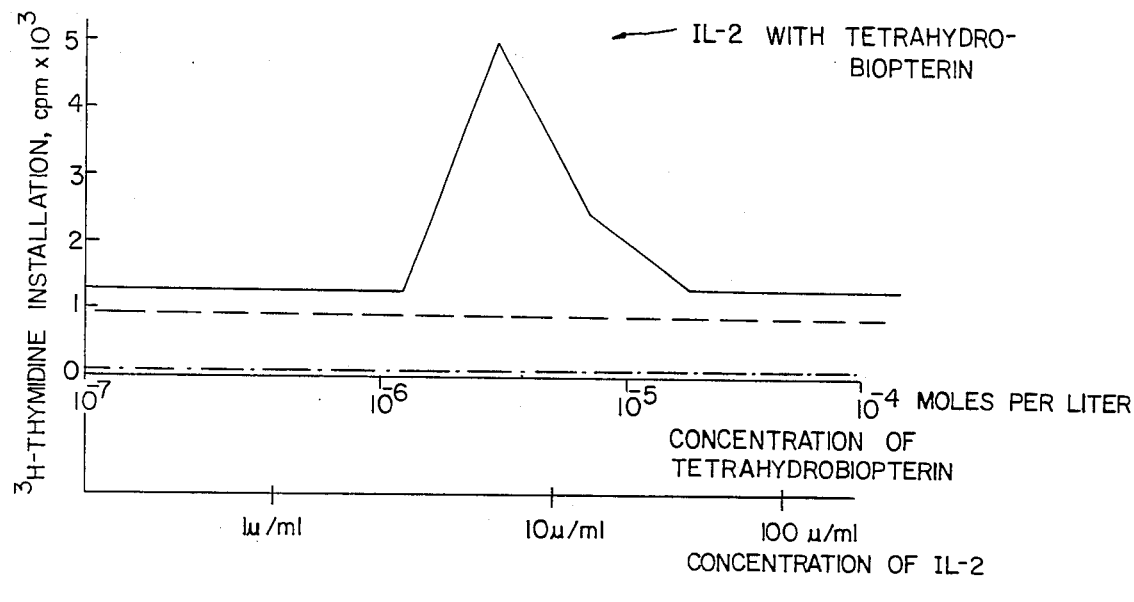

USE OF TETRAHYDROBIOPTERIN TO ENHANCE THE PROLIFERATIVE ACTIVITY OF INTERLEUKIN-2 ON T CELLS

This is a continuation-in-part of application Ser. No. 787,891, filed Oct. 16, 1985, now abandoned.

BACKGROUND OF THE INVENTION

The present invention relates to the use of pterins to increase the in-vivo and in-vitro activity of lymphokines and other blood factors.

Lymphokines are specific substances secreted by lymphocytes in reaction to antigen stimulation. Considered to be intermediates in cell-mediated immunity, they also play a significant part in inflammations, etc. They are not antibodies, but biologically highly active factors (hormones) that are receptor-specific to preferred target cells. Interleukin-2, interleukin-3, CSF (colony-stimulating factor), and B-cell factors, for example, are lymphokines. Since the concepts of immunology, including that of "lymphokines," are always changing as the result of new knowledge, the term "other blood factors" is also to be understood as being included therein.

Interleukin-2, abbreviated IL-2 and previously also called T-cell growth factor (TCGF) (Aarden, L.A. et al., "Revised nomenclature for antigen-nonspecific T-cell proliferation and helper factors," *J. Immunology* 123 [1979], 1928-2929; and Morgan, D. A., Ruscetti, F. W., and Gallo, R. C., "Selective in vitro growth of T lymphocytes from normal human bone marrow," *Science* 193 [1976], 1007), is a glycoprotein with a molecular weight of about 15 000 and an isoelectric point in the neutral range (Gillis, S., Mochizuki, D. Y., Coulon, P. J., Hefeneider, S. H., Rambthun, C. A., Gillis, A. E., Frank, M. B., Henney, C. S., & Watson, J. D., "Molecular characterization of interleukin-2," *Immunolog. Rev.* 63 [1982], 167-209). Its occasionally described molecular heterogeneity is ascribed to differences in glycosylation (Robb, R. J. & Smith, K. A., "Heterogeneity of human T-cell growth factor due to variable glycosylation," *Molecular Immunol.* 18 [1981], 1087-1094).

IL-2 is considered the "second signal" in immunoresponse (Ruscetti, F. W. & Gallo, R. C., "Human T-lymphocyte growth factor: regulation of growth and function of T lymphocytes," *Blood* 57 [1981], 379-394; Wagner, H., Hardt, C., Heeg, K., Pfitzenmaier, K., Solbach, W., Bartlet, R., Stockinger, H., & Röllinghoff, M., "In vivo and in vitro effects of interleukin-2", *Immunol. Rev.* 51 [1980], 215-236) and represents a regulation factor that makes it possible to continuously cultivate normal activated and neoplastic T cells in vitro. Among the effector cells that can be cloned and cultured over the long term with the addition of IL-2 preparations are T-helper and suppressor cells, cytotoxic T cells, and natural killer cells (NKC's).

Many disruptions of the immunodefense system (immunological diseases) can be ascribed to the lack of cells that produce interleukin-2, to inadequate IL-2 production, or to insufficient formation of IL-2 eptors, and can in many cases be improved by prescribing interleukin-2.

More recent studies have also demonstrated that the production of interleukin-2 decreases greatly with age. Interleukin-2 is accordingly an available therapeutic means for curing or moderating diseases that are caused by disruptions in its own production.

Interleukin-2 can also be employed in cancer therapy.

Pterins are described in the literature as animal pigments, as cofactors (tetrahydrobiopterin) in the hydroxylation of tryptophan, phnenylalanine, and tyrosine (with absence leading to serious neurological defects and hyperphenylalaninemia), as regulators of cell proliferation (partial replacement of fetal calf serum), and as factors that exert an effect on the immunosystem (Römpps, *Chemie Lexikon*, 7th ed., 2831-2832; Milstein, S. & Kaufman, S., "Tetrahydro-sepiapterin as an intermediate in tetrahydrobiopterin biosynthesis," *Biochemical and Biophysical Research Communications* 115, 3 [Sept. 30, 1983], 888-893; Ziegler, I., Hamm, U., & Berndt, I., "Participation of pterins in the control of lymphocyte stimulation and lymphoblast proliferation," *Cancer Research* 42 [1983], 5356-5359); Ziegler, I., Schwulera, U., Sonneborn, M. H., Muller, W. J. P. "Modulation of Interleukin-2 activity by lymphocyte-derived tetrahydro biopterin," *Naturwissenschaften* 72 (1985), 330-331.

The biological detection of lymphokines is often very difficult if they are present in very small amounts, and makes diagnosis difficult. It is also considered worth attempting to increase the effectiveness of lymphokines in therapeutic applications.

SUMMARY OF THE INVENTION

The object of the present invention is to increase both the range of detection of the biological lymphokine test and the in-vitro and in-vivo activity of lymphokines and other blood factors.

This object is attained in accordance with the invention in that pterins are employed in conjunction with lymphokines or in that a pterin is added to a preparation of lymphokines.

Surprisingly, it turns out that adding a pterin to a lymphokine can increase the activity of lymphokines by 3 to 5 times and that pterins accordingly act as lymphokine immunomodulators.

In the case of interleukin-2, the addition in accordance with the invention of a pterin to preparations that contain it makes it possible to increase the range of detection and hence the sensitivity of the test system. Furthermore, the addition of a pterin has a positive effect on the proliferation of activated T cells. In diagnostic interleukin-2 tests as well, the addition in accordance with the invention of a pterin to the ELISA or RIA test kit will increase the range of detection.

Furthermore, the addition of a pterin to therapeutic interleukin-2 preparations will increase activity, i.e. augment the immunodefense system. This result involves increasing the number of activated T cells, inducing IL-2-dependent killer cells and γ-interferon, and affecting the expression of D or Dr antigens.

A positive effect on B cells is also probably exerted.

Although not based on a particular theory, analyses of pterins in activated lymphocytes, and other studies as well, indicate that the presence of a glycoprotein is a prerequisite for the pterin to take effect, as in the case with interleukin-2 in conventionally prepared lymphocytes.

Especially preferred as a pterin in accordance with the invention is tetrahydrobiopterin which, as described in Biochemical and Biophysical Research Communications, Vol. 115, No. 3 (1983) 888, 892, is biosynthesized as follows:

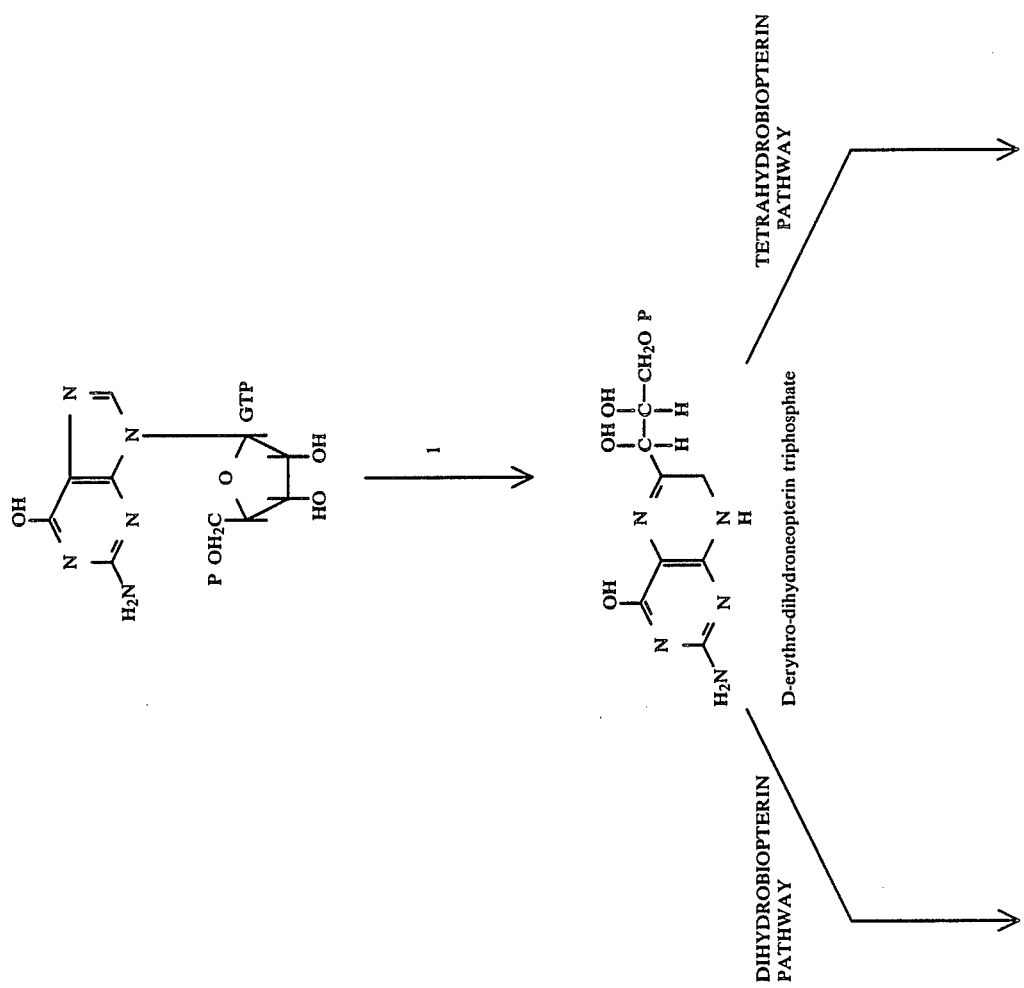

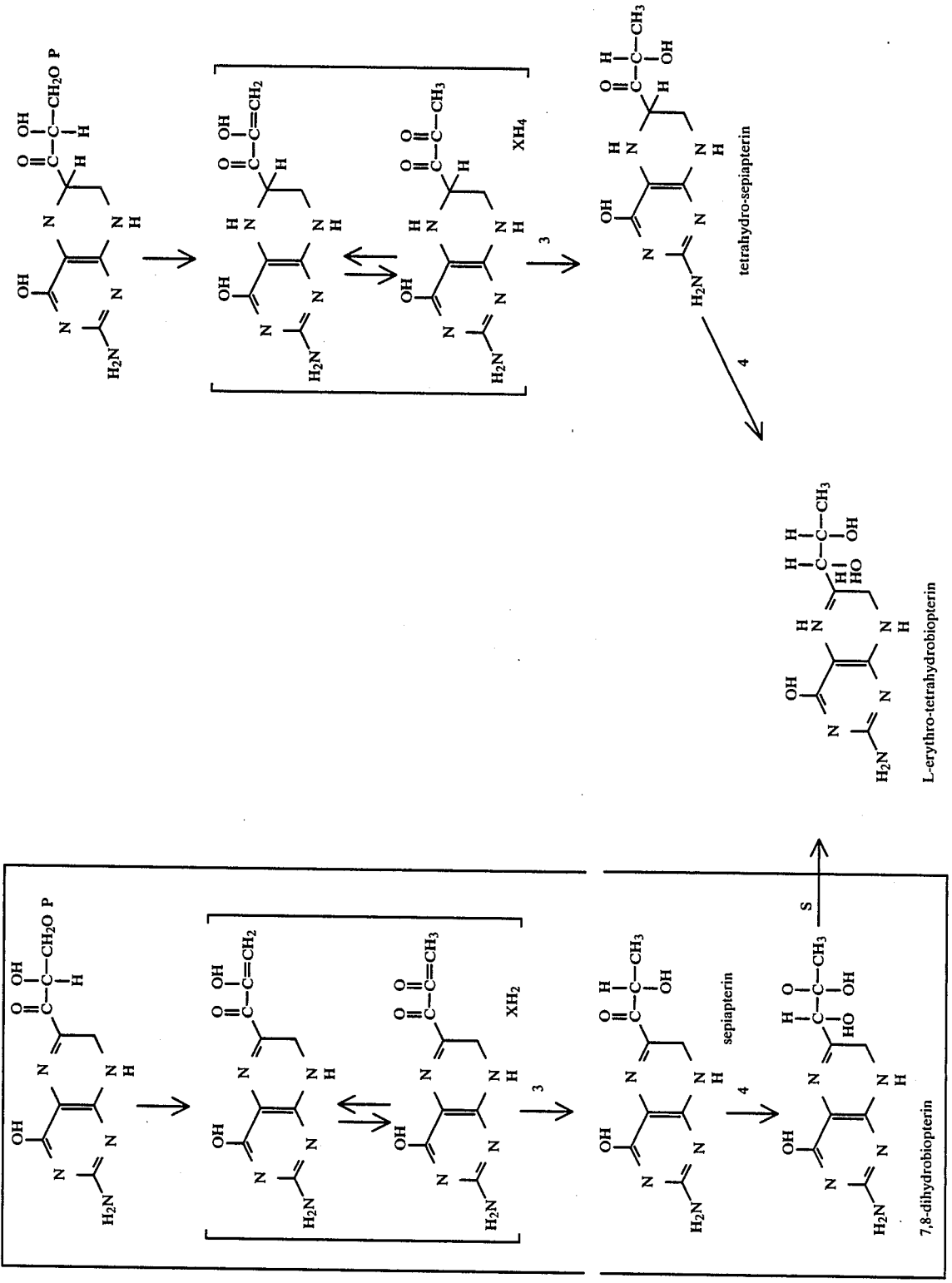

The lymphokine preparations employed for testing the activity-increasing effect of a pterin include raw interleukin-2 (German OS No. 3 149 360, Example 1), partly purified interleukin-2 (German OS 3 149 360 Example 2), highly purified interleukin-2 (Robb, R. J. et al., *Biochem. Biophys. Research COMM* 116 [1983], 1049-1055, where, however, a different antibody, specifically the antibody to interleukin-2 described in German Patent Application P No. 3 329 449.6, is used), and inactive interleukin-2, a batch of active interleukin-2 obtained by the aforesaid method and inactivated as the result of lyophilization.

Surprisingly, not only is the activity of the active preparations increased in accordance with the invention, but products that have become inactive during the course of preparation will again be useful.

The increase in the activity of lymphokines, especially of interleukin-2, was demonstrable with interleukin-2-dependent cytotoxic T-cell indicator lines in the mouse as well as with mouse-spleen lymphocytes or human lymphocytes (mononuclear cells) stimulated with ConA or PHA as indicator cells.

The degree of $^3$H-thymidine incorporation was employed as a sign of increased activity.

The whole series of tests indicated that optimal results are obtained at a pterin concentration of about $10^{-6}$ to $10^{-5}$ moles per liter and an interleukin-2 concentration of about 1 to 20 units per ml.

The number of units of interleukin-2 activity is computed from comparison with the provisional International Standard. The provisional International Reference Unit for interleukin-2 is described in Lymphocin Research, 3rd ed., 1984.

BRIEF DESCRIPTION OF THE DRAWING

The invention will be further described with reference to the accompanying drawing which is a plot of concentration of tetrahydrobiopterin and IL-2 against $^3$H-thymidine activity.

EXAMPLES

The following tests were conducted to demonstrate the effect of pterins on the activity of lymphokines. All work was carried out under red light due to the sensitivity to light of tetrahydrobiopterin.

Example 1

A. Manufacturing PHA blasts 2000 IE of sodium heparin were added to 100 ml of whole blood to prevent coagulation. The mononuclear cells (MNC) were isolated (400×g, 20 min.) through a gradient over Ficoli Hypaque (1:1). After being washed, the cells were stimulated with 0.5 μg of PHA per ml for 72 hours.

| Batch | |
|---|---|
| 0.8 × 10$^6$ MNC/ml | |
| 0.5 μg PHA/ml | |
| 10% FCS | (Cancer Research 43 |
| 100 U penicillin/ml | [1983] 5356–5359 |
| 100 μg streptomycin/ml | and |
| 37° C. | Naturwiss. 72 (1985), |
| 6% CO$_2$ | 330–331) |
| in RPMI 1640 | |

(Similar results can be achieved using up to 9.5 μg PHA/ml or 2.5 μg ConA/ml).

The blasts were then centrifuged off, washed, and incubated as above for 6 more hours. This was followed again by centrifuging.

B.

The cells obtained in Stage A were taken up in the medium described with reference to Stage A, to which 10% FCS had also been added. 100 μm of an interleukin-2 preparation manufactured as described in German OS No. 3 149 360, Example 4 were treated with 100 μl of an aqueous solution of tetrahydrobiopterin (1 μg per 10 μl of medium or 10 μl of IL-2) and serially diluted by ½ in the medium. 100 μl of cells were treated with 100 μl of the serial dilution of tetrahydrobiopterin in the medium or IL-2. The foregoing preparations were incubated for 12 hours at 37° C. in 5% CO$_2$. Finally, they were pulsed for 3 hours with 2 μCi of $^3$H-thymidine each, harvested, and counted in a β counter.

The results of this test indicated that tetrahydrobiopterin is inactive in relation to the indicator cells when added to the medium alone. Combining the interleukin-2 with the tetrahydrobiopterin, however, leads to as much as a 5-fold increase in $^3$H-thymidine incorporation over the basic interleukin-2 value. Combining various concentrations of interleukin-2 with various concentrations of tetrahydrobiopterin indicated that optimal cooperation definitely depends on the concentration of both partners.

An optimal effect was obtained at a tetrahydrobiopterin concentration of $10^{-6}$ to $10^{-5}$ moles per liter and an interleukin-2 concentration of 1 to 20 units per ml in terms of the provisional International Standard.

Example 2

A.

Mouse-spleen cells were stimulated with ConA by the method described in Ziegler, Hamm & Berndt, supra.

B.

The cells obtained in Stage A were treated as described with reference to Example 1, Stage B.

The results were qualitatively identical to those of Example 1.

Example 3

An interleukin-2-dependent cytotoxic T-cell indicator line was taken up into the medium described with reference to Example 1, B and treated as described therein.

The results were almost identical to those described with reference to Example 1.

Example 4

The procedure was identical with those of Examples 1, 2, and 3 except that highly purified, raw, and inactivated interleukin-2 respectively were employed as lymphokine preparations.

The drawing is an extrapolation from all the examples and confirms what has been said in relation to Example 1.

It is understood that the specification and examples are illustrative but not limitative of the present invention and that other embodiments within the spirit and scope of the invention will suggest themselves to those skilled in the art.

We claim:

1. A composition consisting essentially of interleukin-2 and tetrahydrobiopterin, said tetrahydrobiopterin being present in an amount sufficient to increase the proliferative activity of the interleukin-2 on T cells as evidenced by enhanced $^3$H-thymidine incorporation into said T cells.

2. The composition according to claim 1, wherein the interleukin-2 is present in about 1 to 20 units per ml and the tetrahydrobiopterin is present in about $10^{-6}$ to $10^{-5}$ moles per liter.

3. In the method of causing proliferation of antigen or mitogen-stimulated T cells in vitro by adding interleukin-2 to said T cells, the improvement which comprises adding tetrahydrobiopterin in an amount sufficient to increase the proliferative activity of the interleukin-2 as evidenced by enhanced $^3$H-thymidine incorporation into said T cells.

4. The method according to claim 3, wherein the interleukin-2 is present in about 1 to 20 units per ml and the tetrahydrobiopterin is present in about $10^{-6}$ to $10^{-5}$ moles per liter.

* * * * *